United States Patent
Illanes Manriquez et al.

(10) Patent No.: US 11,918,380 B2
(45) Date of Patent: Mar. 5, 2024

(54) MINIMALLY INVASIVE EXAMINATION DEVICE

(71) Applicant: Surag Medical GmbH., Magdeburg (DE)

(72) Inventors: Alfredo Illanes Manriquez, Magdeburg (DE); Michael Friebe, Recklinghausen (DE); Axel Boese, Magdeburg (DE); Ali Pashazadeh, Magdeburg (DE); Ivan Maldonado Zambrano, Magdebur (DE)

(73) Assignee: Surag Medical GmbH., Magdeburg (DE)

( * ) Notice: Subject to any disclaimer, the term of this patent is extended or adjusted under 35 U.S.C. 154(b) by 670 days.

(21) Appl. No.: 16/644,507

(22) PCT Filed: Jun. 26, 2018

(86) PCT No.: PCT/EP2018/067156
§ 371 (c)(1),
(2) Date: Mar. 5, 2020

(87) PCT Pub. No.: WO2019/002318
PCT Pub. Date: Jan. 3, 2019

(65) Prior Publication Data
US 2020/0229764 A1    Jul. 23, 2020

(30) Foreign Application Priority Data
Jun. 26, 2017 (DE) ...................... 10 2017 114 077.8

(51) Int. Cl.
*A61B 5/00* (2006.01)
*A61B 5/06* (2006.01)
*A61B 10/02* (2006.01)

(52) U.S. Cl.
CPC ............ *A61B 5/6847* (2013.01); *A61B 5/065* (2013.01); *A61B 5/067* (2013.01); *A61B 10/0233* (2013.01)

(58) Field of Classification Search
CPC ... A61B 17/3403; A61B 5/6847; A61B 5/065; A61B 5/067; A61B 10/0233;
(Continued)

(56) References Cited

U.S. PATENT DOCUMENTS 6,705,319 B1 * 3/2004 Wodicka ........... A61M 16/0488
128/207.14
2003/0040737 A1  2/2003 Merril et al.
(Continued)

FOREIGN PATENT DOCUMENTS

WO  WO 2017/145141  8/2017
WO  WO 2019/002318  1/2019

OTHER PUBLICATIONS

Girault, J-M., et al. "Time-varying autoregressive spectral estimation for ultrasound attenuation in tissue characterization." IEEE transactions on ultrasonics, ferroelectrics, and frequency control 45.3 (1998): 650-659. (Year: 1998).*

(Continued)

*Primary Examiner* — Sean D Mattson

(57) ABSTRACT

A minimally invasive examination device for assisting in the positioning of an interventional instrument in the body of a patient. The device allows improved positioning of an interventional instrument in the body of a patient. The device comprises:
  a coupling element on which at least one first sensor is arranged and that is coupled to a proximal end of the interventional instrument, as a result of which the first sensor is connected to the interventional instrument (16) via the coupling element,
  a signal detection and processing device that is connected to the first sensor in a wireless or wired manner so as to transmit signals, wherein the signal detection and processing device (20, 34) is designed to process the signals from the first sensor, and
  a display device that is designed to visually display processing results from the signal detection and processing device.

9 Claims, 3 Drawing Sheets

(58) Field of Classification Search
CPC .................. A61B 2017/3405–3413; A61B 2034/2046–2065; A61M 2025/0166
See application file for complete search history.

(56) References Cited

U.S. PATENT DOCUMENTS

| | | | | |
|---|---|---|---|---|
| 2011/0060229 A1* | 3/2011 | Hulvershorn | .......... | A61B 5/339 600/561 |
| 2011/0230906 A1* | 9/2011 | Modesitt | .......... | A61B 1/04 606/185 |
| 2011/0270083 A1* | 11/2011 | Shen | .......... | A61B 5/7203 600/424 |
| 2013/0296693 A1 | 11/2013 | Wenzel et al. | | |
| 2014/0171792 A1* | 6/2014 | Dalal | .......... | A61B 17/3403 600/424 |
| 2015/0080711 A1* | 3/2015 | Hendriks | .......... | A61B 6/5217 600/424 |
| 2015/0208942 A1* | 7/2015 | Bar-Tal | .......... | A61B 34/20 600/509 |
| 2016/0100852 A1* | 4/2016 | Hyde | .......... | A61B 5/0077 600/309 |
| 2017/0172507 A1* | 6/2017 | Sipple | .......... | A61B 5/7405 |

OTHER PUBLICATIONS

Internationaler Recherchenbericht und Schriftlicher Bescheid [International Search Report and the Written Opinion] dated Nov. 16, 2018 From the International Searching Authority Re. Application No. PCT/EP2018/067156 and its Translation Into English. (14 Pages).

* cited by examiner

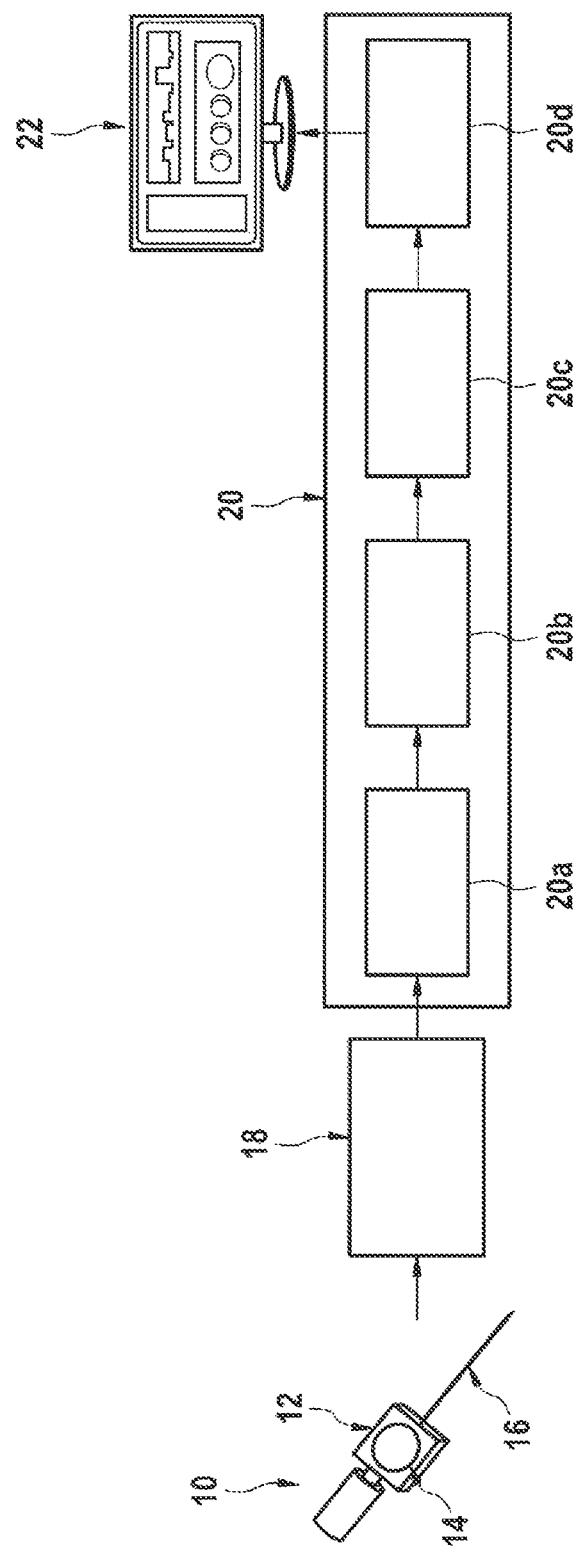

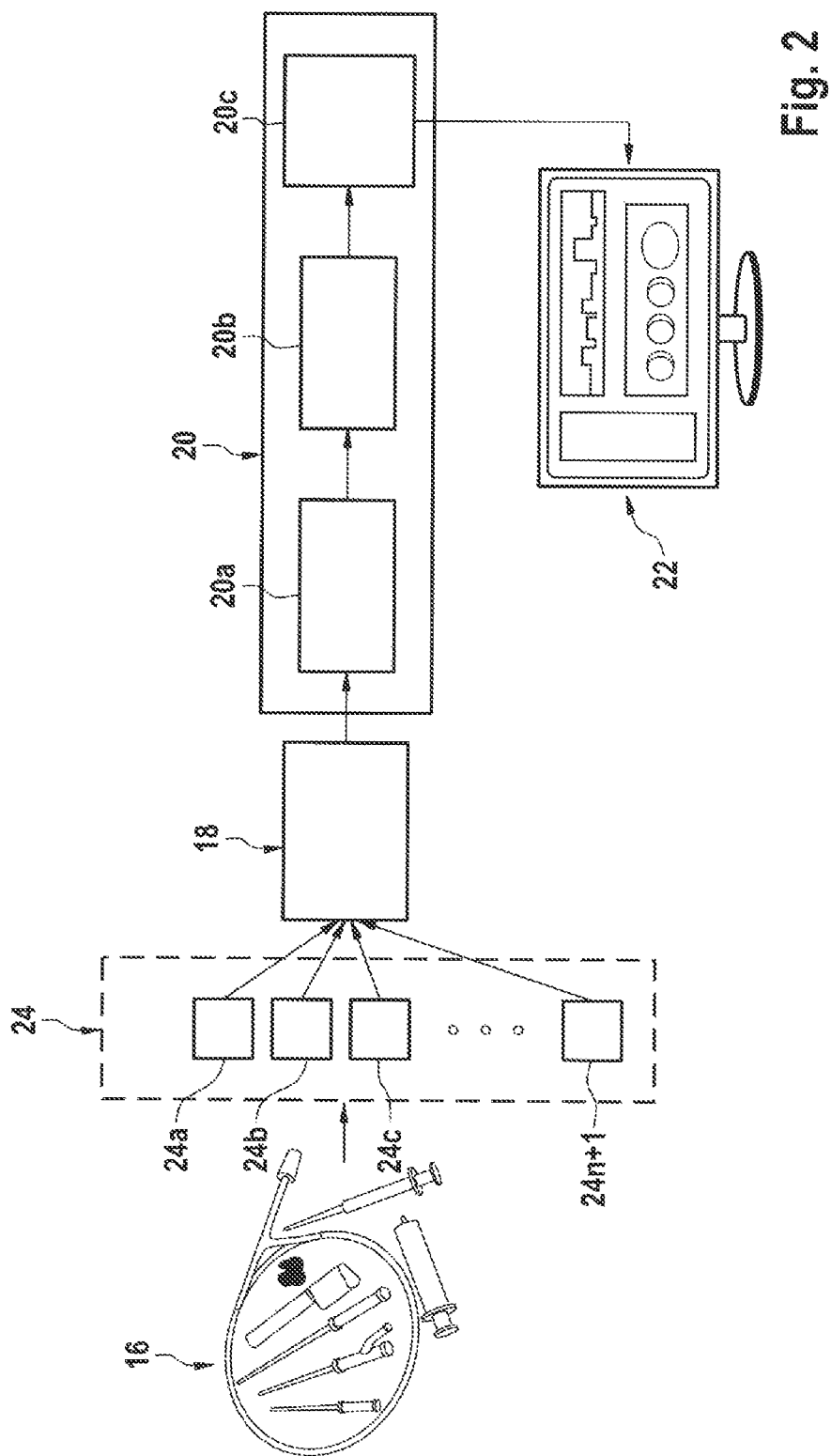

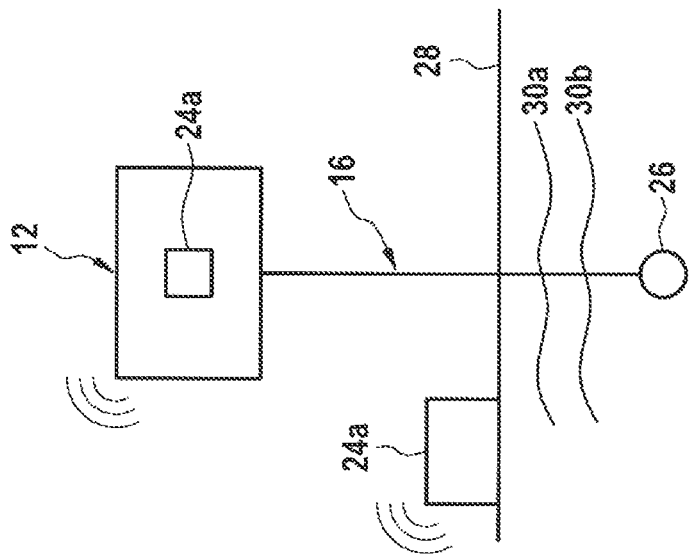
Fig. 4
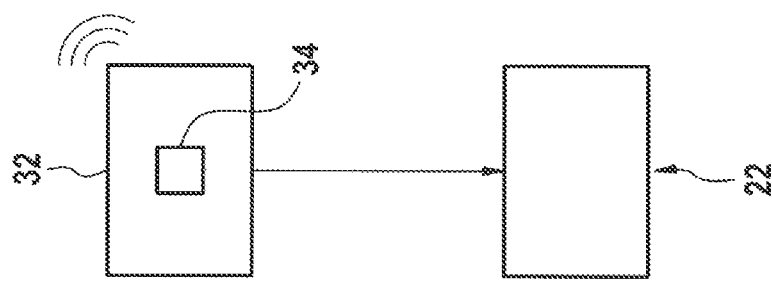
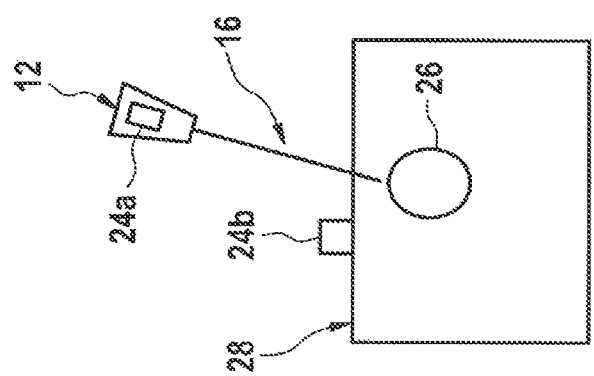
Fig. 3

MINIMALLY INVASIVE EXAMINATION DEVICE

RELATED APPLICATIONS

This application is a National Phase of PCT Patent Application No. PCT/EP2018/067156 having International filing date of Jun. 26, 2018, which claims the benefit of priority of German Patent Application No. 10 2017 114 077.8 filed on Jun. 26, 2017. The contents of the above applications are all incorporated by reference as if fully set forth herein in their entirety.

FIELD AND BACKGROUND OF THE INVENTION

The invention relates to a minimally invasive examination device for assisting in the positioning of an interventional instrument in or on the body of a patient, in particular for diagnostic or therapeutic purposes.

The invention furthermore relates to a method for determining the advancement and/or the position of an interventional instrument in the body of a patient using such an examination device.

The use of instruments used in an interventional manner ("medical interventional devices", MID for short) is nowadays common in medicine in the field of minimally invasive procedures. Interventional instruments may be for example needles, tools, endoscopes, catheters or guide wires.

By way of example, percutaneous needle insertion is one of the most common applications in minimally invasive medicine. Many medical treatment methods involve the insertion of needles (for example biopsy needles) in order to make a diagnosis or perform a therapy. These minimally invasive procedures comprise for example biopsy, brachytherapy, regional anesthesia, and radiofrequency ablation.

In all of these procedures, it is necessary for the user (for example a surgeon) to insert the interventional instrument into the body of the patient and to guide it to a target site and/or to follow a predetermined path to the target site without injuring vital organs or structures in the process. A percutaneous needle insertion into soft tissue or a guide wire trajectory are examples of this. Performing such a measure is not easy. The interventional instrument is often inserted deep into the body, and the target site is often only a few millimeters from other organs, vessels or nerves, injury to which should be avoided. The main causes of inaccurate placement of an interventional instrument are the shifting of the target site due to soft tissue deformation, deflection of the needle due to needle-tissue interaction, patient movement, and physiological changes to the organ in question between planning and performing the intervention.

The trajectory of the interventional instrument is not able to be tracked visually, or is able to be tracked visually only to an insufficient extent. For instrument guidance, diagnostic (mainly imaging) systems are therefore additionally used, or the trajectory is planned using a diagnostic image captured before the intervention.

A real-time display in order to navigate the interventional instrument in the body of the patient may improve quality and safety when performing the intervention, in combination with the surgeon's experience and knowledge. Such a display may be achieved for example using computed tomography, CT for short, ultrasound, US for short, or magnetic resonance, MRI for short. However, all of these methods also have disadvantages for example in terms of the display and resolution of the image used for navigation. A further disadvantage is that comparatively complex and expensive imaging methods have to be used. A further disadvantage is that these methods do not always indicate the exact position of the instrument due to image artefacts and other physical effects. It may thus for example be the case that the methods indicate a position in a structure within the body, but the instrument is in fact still or once again outside this structure.

SUMMARY OF THE INVENTION

One object of the invention is therefore to provide a device that allows improved positioning of an interventional instrument in the body of a patient.

This object is achieved by the invention by way of a minimally invasive examination device for assisting in the positioning of an interventional instrument in the body of a patient, comprising:
- a coupling element on which at least one first sensor is arranged and that is coupled to a proximal end of the interventional instrument, as a result of which the first sensor is connected to the interventional instrument via the coupling element,
- a signal detection and processing device that is connected to the first sensor in a wireless or wired manner so as to transmit signals, wherein the signal detection and processing device is designed to process the signals from the first sensor, and
- a display device that is designed to visually display processing results from the signal detection and processing device.

Using the minimally invasive examination device according to the invention, it may be made possible to determine the position of the interventional instrument in the body of the patient. The sensor that is used may be coupled to the proximal end, that is to say the end of the instrument facing the user, via the coupling element. The instrument therefore does not need to be specifically adapted to the use according to the invention. The instrument is used in the usual way.

The sensor coupled to the interventional instrument according to the invention responds to the interaction between the interventional instrument and the tissue. By way of example, forces are developed when a needle is inserted into soft tissue. Forces furthermore arise when the needle shaft is guided through different layers of tissue, for example skin, muscles and fat. These mechanical interactions are influenced by many factors, for example by characteristics of the needle and the tissue, insertion rate, direction of insertion, etc. According to the invention, use is in this case made of the fact that the mechanical interactions are transmitted as measurable signals via the interventional instrument to the proximal end thereof and are able to be detected there by the sensor via the coupling element.

The detected sensor signals are detected by way of the signal detection and processing device and subsequently digitally processed, for example by way of a computer that analyzes the data, as far as possible in real time, and derives the relevant parameters for the positioning of the interventional instrument from the data.

According to the invention, the processing results from the signal detection and processing device are displayed visually by way of the display device. As a result, the surgeon guiding the interventional instrument is able to be given feedback from which he is able to ascertain for example whether the interventional instrument has penetrated certain different layers of tissue. The display may furthermore indicate to the surgeon whether the interventional instrument has reached the target site in the body of the patient, for example by using the sensor signals—more reliably than would be possible manually—to identify the different mechanical advancement resistances in the soft tissue. The feedback may allow the surgeon to recognize a transition between organs and cavities in the body and also to identify the differences between the tissue properties. As a result, undesired tissue damage or damage to other structures along the path of the interventional instrument in the body is able to be avoided, and it is additionally able to be ensured that the planned target site is actually reached. This is of great importance, especially for tissue removal (biopsies).

The first sensor is preferably a sound detection sensor, in particular a microphone or stethoscope, wherein the coupling element connects the interventional instrument to the first sensor so as to transmit sound. The audio signals that are created firstly at the distal end of the medical device when the interventional instrument is inserted into the body and when it passes through the body to the target point and are then transmitted—as a structure-borne sound—through the instrument to the sensor at the proximal end are thereby able to be detected. The audio signals may be processed in various ways and converted into a visual representation. In the simplest case, the digital time signal in which for example characteristic peaks of the audio signal are visible is displayed, or the spectrum of the audio signal and the temporal change thereof may be displayed in a suitable manner in order thereby to discern characteristic changes during the advancement of the instrument through different layers of tissue.

In a further preferred embodiment, the first sensor is an acceleration sensor, gyroscope, force sensor, friction sensor, vibration sensor, pressure sensor or laser-based sensor. Mechanical variables, for example vibrations of the instrument, are able to be detected in a very sensitive manner by way of the laser-based sensor, for example through interferometry. The laser-based sensor may also perform a distance measurement to a reference point in order to detect the depth of advancement of the instrument in the body. Various types of mechanical measured variables that provide information about the course of the movement as the instrument advances are able to be detected and visually processed by way of the various sensors.

It is preferred for the minimally invasive examination device to comprise at least one second sensor. Several different signals are thereby able to be detected and visually processed. The second sensor may in this case likewise be a sound detection sensor, an acceleration sensor, gyroscope, force sensor, friction sensor, vibration sensor, pressure sensor or laser-based sensor. The minimally invasive examination device may furthermore comprise more than two sensors. By combining two or more sensors, redundancy may be achieved and/or a plausibility check may be performed during the position determination, in order thereby to increase reliability and accuracy.

In one preferred embodiment, the at least one second sensor is arranged on the body of the patient. The second sensor is thus not connected to the interventional instrument via the coupling element. As a result of the arrangement on the body, mechanical measured variables (for example in the form of a sound signal) may also be detected, analyzed and visually displayed there during the guidance of the interventional instrument.

In a further preferred embodiment, a sound or vibration generator, for example in the form of a speaker, is provided, the signal from which is introduced into the body of the patient. The frequency of the signal generated by the sound or vibration generator is preferably in the low-frequency acoustic range, that is to say between 1 Hz and 20 kHz, preferably between 1 Hz and 5 kHz. For this purpose, the sound or vibration generator may likewise be arranged proximally on the interventional instrument, preferably via the coupling element. Alternatively, the sound or vibration generator may be arranged separately from the interventional instrument directly on the body of the patient. The sound or vibration generator generates a sound or vibration signal that excites the body tissue according to oscillations or vibrations. In this case, the signal detection and processing device is expediently designed to analyze the modification, brought about by particular different layers of tissue, of the oscillation or vibration signal detected via the interventional instrument and the at least one sensor (that is to say as it were the acoustic impedance of the tissue) and to generate visual feedback that allows the surgeon to recognize a transition between organs and cavities in the body and also to identify the differences between the tissue properties. It is thereby for example able to be ensured that the planned target site is actually reached. The frequency of the sound or vibration generator is preferably tunable. Alternatively, the sound or vibration generator generates a signal with a sufficiently broad spectrum (noise) such that corresponding spectral analysis of the response signal detected via the at least one sensor is able to be performed by way of the signal detection and processing device. The reliability and accuracy in distinguishing between different types of tissue penetrated by the interventional instrument during the advancement is thereby able to be further improved.

The invention furthermore relates to a method for determining the advancement position of an interventional instrument in the body of a patient using an examination device according to the invention. The method comprises the following steps:

detecting a sensor signal from the at least one first sensor,
processing the sensor signals by way of the signal detection and processing device, and
displaying the processing results by way of the display device.

According to the invention, the advancement position of the interventional instrument is able to be derived from the sensor signal detected during the advancement of the interventional instrument in the body of the patient, for example by detecting the time at which (or the time intervals during which) the energy distribution of the sensor signal over two or more different frequency bands changes during the advancement of the instrument. Corresponding changes may be associated for example with the transition of a needle tip of the interventional instrument from a layer of tissue into a following layer of tissue during the advancement.

In one preferred embodiment, the processing of the sensor signals comprises time-frequency analysis of the (digital) sensor signals, for example by way of a wavelet transformation or wavelet decomposition. Wavelet analysis is known from the prior art as a tool for characterizing time-frequency signals. In this case, the temporally changeable sensor signal is represented by its decomposition into wavelets. Evaluating the wavelet coefficients resulting from the wavelet transformation or decomposition makes it possible to calculate the instantaneous energy or power of the sensor signal in a particular frequency band.

Alternatively or additionally, it is possible for the processing of the sensor signals to comprise time-frequency analysis by way of time-variable autoregressive modeling. Autoregressive modeling is known from the prior art. In signal processing, an autoregressive model is a representation of random processes. It is used to describe time-variable processes (the sensor signal in the context of the invention). The autoregressive model determines that the instantaneous value of the sensor signal depends linearly on its own previous values and on a stochastic term. The temporal variation of the sensor signal is able to be determined by deriving temporally changeable poles of the spectrum resulting from the modeling. The advancement position of the interventional instrument may also be determined therefrom according to the invention, for example by observing how the spectral positions of the poles change during the advancement of the instrument.

BRIEF DESCRIPTION OF THE SEVERAL VIEWS OF THE DRAWINGS

Exemplary embodiments of the invention will be explained in more detail below with reference to the figures. In the figures:

FIG. 1 shows a first embodiment of a minimally invasive examination device and an associated method flowchart;

FIG. 2 shows a second embodiment of the minimally invasive examination device and an associated method flowchart;

FIG. 3 shows a schematic detailed view of a third embodiment of the minimally invasive examination device when examining a target site;

FIG. 4 shows a schematic illustration of the progression of an examination of a target site using the third embodiment of the minimally invasive examination device.

In the following description of the figures, the same reference signs and the same terms are used for the same elements.

DESCRIPTION OF SPECIFIC EMBODIMENTS OF THE INVENTION

FIG. 1 shows a first embodiment of a minimally invasive examination device 10 according to the invention and an associated method flowchart of the processing and visual representation of detected signals. The minimally invasive examination device 10 in this exemplary embodiment comprises a needle 16 as interventional instrument. A coupling element 12 is arranged at the proximal end of the needle 16. The coupling element 12 has a connection for a first sensor 14. The first sensor 14 is a stethoscope in this exemplary embodiment. The first sensor 14 is connected to the interventional instrument 16 via the coupling element 12 so as to transmit sound.

FIG. 1 also illustrates the method steps from the signal detection to the visual output of the detected and processed sensor signals. Before the detected signals are forwarded to a signal detection and processing device 20, analog amplification and filtering of the signals may take place. This is indicated by box 18. The following method steps are performed in the signal detection and processing device 20: In box 20a, a signal detection takes place (for example through digitization). After detection, the signals are preprocessed in box 20b. This may be performed for example by way of linear filtering. This is followed by extraction of time-variant parameters, for example by calculating the temporally changeable frequency components of the sound signal from the stethoscope. This is symbolized by box 20c. The signals are then classified in box 20d, for example using a neural network. After the signal processing in the signal detection and processing device 20, the processed signals are appropriately converted into a video output signal and displayed visually on a display device 22. For example, in one illustration in the form of a graph, the dominant frequency components of the detected signal may be displayed as a function of time. When the instrument 16 penetrates different layers of tissue, the frequency components change, this being immediately recognizable in the graph.

Using the signal detection and processing device 20, which is connected in a wireless or wired manner to the proximal end of the medical device 16, may thus provide a surgeon with visual feedback about the position of the interventional instrument 16 in the body of a patient in the case of a minimally invasive intervention.

FIG. 2 illustrates a second embodiment of the minimally invasive examination device according to the invention and an associated method flowchart. In contrast to FIG. 2, in this exemplary embodiment, the minimally invasive examination device has a housing 24 as coupling element, in which a plurality of sensors 24a, 24b, 24c, 24n+1 are arranged. The exact arrangement of the housing 24 on the interventional instrument 16 is not illustrated in FIG. 2, but the housing 24 should be arranged at the proximal end of the interventional instrument 16, as in FIG. 1. The reference sign 24n+1 is intended here to indicate any desired number of sensors. The sensors 24a, 24b, 24c, 24n+1 may in this case represent identical or different sensors. By way of example, the sensor 24a may be a sound detection sensor, the sensor 24b may be an acceleration sensor, and the sensor 24c may be a gyroscope. The sensor data detected by the sensors 24a, 24b, 24c, 24n+1 are then processed and evaluated again in a signal detection and processing device 20. The method steps are again illustrated symbolically as boxes 18, 20a, 20b, 20c. The method steps are identical to the method steps of FIG. 1, with the difference that the signals from the various sensors 24a-24n+1 are processed in parallel.

FIG. 3 is a schematic view of a third embodiment of a minimally invasive examination device in the case of examining a target site 26 in the body 28 of a patient. This third embodiment has two sensors 24a, 24b. A first sensor 24 is arranged on the coupling element 12. The coupling element 12 is arranged at the proximal end of the interventional instrument 16. It may furthermore be seen that the distal end of the interventional instrument 16 is located in the body 28 and has almost reached the target site 26. The second sensor 24b is located on the surface of the body 28 in this exemplary embodiment. The sensors are thereby able to detect different, complementary signals, which are able to be forwarded to a signal detection and processing device, not shown here, in order to determine, as accurately as possible, the position of the distal end of the interventional instrument 16 within the body 28. By way of example, the signals from the sensors 24a and 24b may be used in combination to determine whether the distal end has reached the target site 26. The sensor 24b may in this case likewise be connected to the coupling element 12 via a cable in order to transmit the signals to the signal detection and processing device, not illustrated, via the coupling element 12. The signals from both sensors 24a, 24b, which may again be for example sound detection sensors, are processed and displayed such that the surgeon is able for example to recognize, on the basis of coincidence of the signals, that the instrument 16 has reached the target site 26.

FIG. 4 shows a schematic illustration of the progression of an examination of the target site 26 using the third embodiment of the minimally invasive examination device. As in FIG. 3, a first sensor 24a is arranged in the coupling element 12 at the proximal end of the interventional instrument 16. A second sensor 24b is arranged on the surface of the body 28. It may also be seen that the interventional instrument 16 has penetrated to the target site 26. In this case, the interventional instrument 16 has penetrated two layers of tissue 30a, 30b. The signals from the sensors 24a, 24 that are detected in this case are transmitted wirelessly to an external server 32 as signal detection and processing device. There, the signals are processed and evaluated and converted into a visual signal or visual representation as described above. This visual signal or visual representation is forwarded to a display device 22.

What is claimed is:

1. A minimally invasive examination device for assisting in positioning of an interventional instrument (16) in or on a body of a patient, comprising:
   a coupling element (12, 24) on which at least a first sensor (14, 24a, 24b, 24c, 24n+1) is arranged and that is coupled to a proximal end of the interventional instrument (16), as a result of which the first sensor (14, 24a, 24b, 24c, 24n+1) is connected to the interventional instrument (16) via the coupling element (12, 24),
   a signal detection and processing device (20, 34) that is connected to the first sensor (14, 24a, 24b, 24c, 24n+1) in a wireless or wired manner so as to transmit signals, wherein the signal detection and processing device (20, 34) is designed to process the signals transmitted from the first sensor (14, 24a, 24b, 24c, 24n+1), and
   a display device (22) that is designed to visually display processing results from the signal detection and processing device (20, 34), wherein the first sensor (14, 24a, 24b, 24c, 24n+1) is a sound detection sensor, and wherein the coupling element (12, 24) connects the interventional instrument (16) to the first sensor (14, 24a, 24b, 24c, 24n+1) so as to transmit sound from the interventional instrument (16) to the first sensor (14, 24a, 24b, 24c, 24n+1); and
   wherein audio signals transmitted through the interventional instrument (16) to the first sensor (14, 24a, 24b, 24c, 24n+1) at the proximal end of the interventional instrument (16) are detected by the first sensor (14, 24a, 24b, 24c, 24n+1), wherein the audio signals are processed and converted into a visual representation, wherein a spectrum of the audio signals and a temporal change thereof is displayed;
   wherein the signal detection and processing device (20, 34) is configured so as to detect a change in a spectral distribution of one of the audio signals from the first sensor (14, 24a, 24b, 24c, 24n+1) over two or more different frequency bands.

2. The minimally invasive examination device as claimed in claim 1, wherein the first sensor (14, 24a, 24b, 24c, 24n+1) is a microphone or stethoscope.

3. The minimally invasive examination device as claimed in claim 1, wherein the minimally invasive examination device comprises at least a second sensor (24a, 24b, 24c, 24n+1).

4. The minimally invasive examination device as claimed in claim 3, wherein the second sensor (24a, 24b, 24c, 24n+1) is designed to be arranged on the body of the patient.

5. The minimally invasive examination device as claimed in claim 1, wherein the interventional instrument (16) is a needle, a biopsy needle, a catheter, a tool, an endoscope or a guide wire.

6. The minimally invasive examination device as claimed in claim 1, further comprising a sound or vibration generator, a signal from which is able to be introduced into the body of the patient.

7. A method for determining a position of the interventional instrument (16) using the examination device as claimed in claim 1, at least comprising the steps of:
   detecting a sensor signal from the first sensor (14, 24a, 24b, 24c, 24n+1),
   processing the sensor signal by way of the signal detection and processing device (20, 34), and
   displaying the processed sensor signal by way of the display device (22).

8. The method as claimed in claim 7, wherein the processing of the sensor signal comprises time-frequency analysis of the sensor signal by way of a wavelet transformation or wavelet decomposition.

9. The method as claimed in claim 7, wherein the processing of the sensor signal comprises time-frequency analysis of the sensor signal by way of time-variable autoregressive modeling.

* * * * *